(12) United States Patent
Rowley

(10) Patent No.: US 11,813,397 B2
(45) Date of Patent: Nov. 14, 2023

(54) NEBULIZER WITH FLUTTER VALVE

(71) Applicant: Justin Rowley, Edmond, OK (US)

(72) Inventor: Justin Rowley, Edmond, OK (US)

( * ) Notice: Subject to any disclaimer, the term of this patent is extended or adjusted under 35 U.S.C. 154(b) by 627 days.

(21) Appl. No.: 16/898,762

(22) Filed: Jun. 11, 2020

(65) Prior Publication Data

US 2020/0390985 A1 Dec. 17, 2020

Related U.S. Application Data

(60) Provisional application No. 62/859,981, filed on Jun. 11, 2019.

(51) Int. Cl.
*A61M 11/04* (2006.01)

(52) U.S. Cl.
CPC ......... *A61M 11/04* (2013.01); *A61M 2205/10* (2013.01); *A61M 2205/3584* (2013.01); *A61M 2205/587* (2013.01); *A61M 2205/75* (2013.01); *A61M 2205/8206* (2013.01)

(58) Field of Classification Search
CPC ...... A61M 11/00; A61M 11/05; A61M 11/04; A61M 2205/10; A61M 2205/3584; A61M 2205/587; A61M 2205/75; A61M 2205/8206; A61M 2205/3331; A61M 15/00–0001; A61M 15/0013–0015; A61M 15/002; A61M 16/0006; A61M 16/20; A61M 15/0018; A61M 16/201; A61M 16/208; A61M 11/005; A61M 15/0085; A61M 15/06; A61M 2205/8243; A63B 23/18

See application file for complete search history.

(56) References Cited

U.S. PATENT DOCUMENTS

| 5,261,601 | A | 11/1993 | Ross et al. |
| 5,435,297 | A | 7/1995 | Klein |
| 6,443,146 | B1 | 9/2002 | Voges |
| 6,581,598 | B1 * | 6/2003 | Foran ..................... A63B 23/18 |
| | | | 128/204.19 |

(Continued)

FOREIGN PATENT DOCUMENTS

| KR | 1020170026559 | 3/2017 |
| WO | 2016142773 A2 | 9/2016 |
| WO | 2018203188 A1 | 11/2018 |

*Primary Examiner* — Rachel T Sippel
*Assistant Examiner* — Jacqueline M Pinderski
(74) *Attorney, Agent, or Firm* — DUNLAP CODDING, P.C.

(57) ABSTRACT

A nebulizer has a body, a fluid reservoir, and a flutter valve. The body has a first end that has a mouthpiece, a second end, an aerosol delivery channel extending though the body from the first end to the second end, and a fluid reservoir receiving compartment in communication with the aerosol delivery channel. The fluid reservoir is positioned in the fluid reservoir receiving compartment. The fluid reservoir contains a volume of fluid and has a vibrating mesh disc for delivering the fluid to the aerosol delivery channel in an aerosol form upon the vibrating mesh disc being energized. The flutter valve is positioned in the aerosol delivery channel of the body near the second end of the body. The flutter valve is moveable between a closed position and an open position when the expiratory pressure greater than a predetermined expiratory pressure is exerted on the flutter valve.

20 Claims, 9 Drawing Sheets

(56) References Cited

U.S. PATENT DOCUMENTS

| | | | |
|---|---|---|---|
| 6,851,626 B2 | 2/2005 | Patel et al. | |
| 6,889,687 B1 | 5/2005 | Olsson | |
| 6,983,747 B2 | 1/2006 | Gallem et al. | |
| 8,374,657 B2 * | 2/2013 | Interdonato | H04B 1/385 |
| | | | 455/344 |
| 8,616,195 B2 | 12/2013 | Power et al. | |
| 8,875,697 B2 | 11/2014 | Denyer et al. | |
| 8,910,625 B2 * | 12/2014 | Mullinger | A61M 16/0003 |
| | | | 128/200.14 |
| 9,700,690 B2 | 7/2017 | Poole et al. | |
| 9,913,950 B2 | 3/2018 | Goodman et al. | |
| 10,004,872 B1 * | 6/2018 | Gao | A61M 16/0866 |
| 2002/0029779 A1 * | 3/2002 | Schmidt | A61M 16/208 |
| | | | 128/205.25 |
| 2005/0011514 A1 * | 1/2005 | Power | B05B 17/0607 |
| | | | 128/200.14 |
| 2008/0078383 A1 * | 4/2008 | Richards | A61M 16/209 |
| | | | 128/203.12 |
| 2012/0097164 A1 * | 4/2012 | Rozario | A61M 16/0006 |
| | | | 128/204.25 |
| 2012/0304988 A1 * | 12/2012 | Meyer | A61M 16/0006 |
| | | | 128/204.25 |
| 2015/0165137 A1 | 6/2015 | Mullinger et al. | |
| 2016/0199594 A1 * | 7/2016 | Finger | A61M 15/0085 |
| | | | 128/200.14 |
| 2017/0000963 A1 | 1/2017 | Hearn et al. | |
| 2017/0106155 A1 | 4/2017 | Reed et al. | |
| 2017/0136205 A1 | 5/2017 | Rusher | |
| 2017/0368273 A1 | 12/2017 | Rubin | |

\* cited by examiner

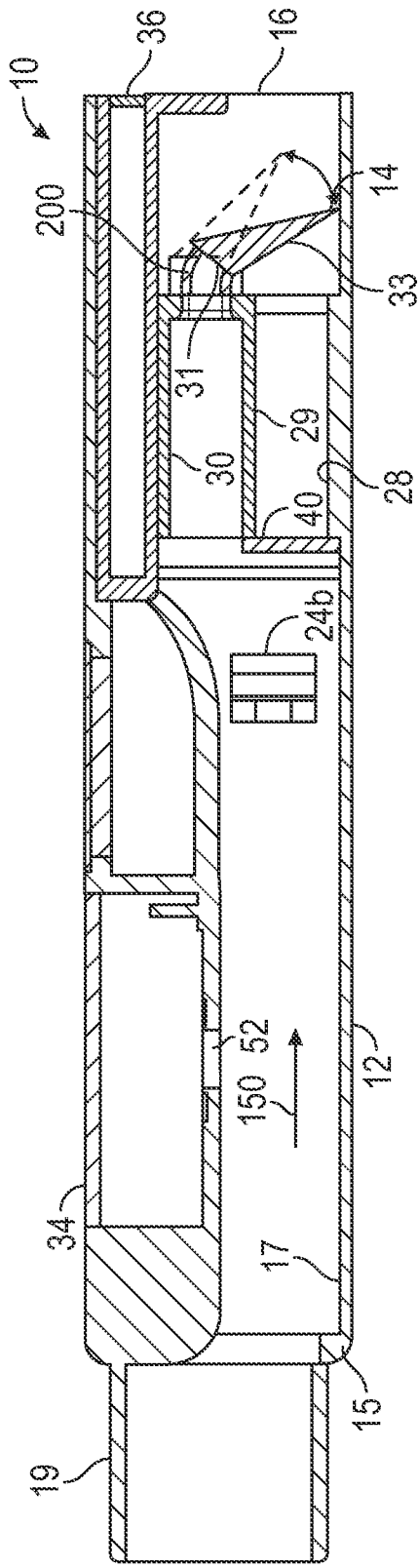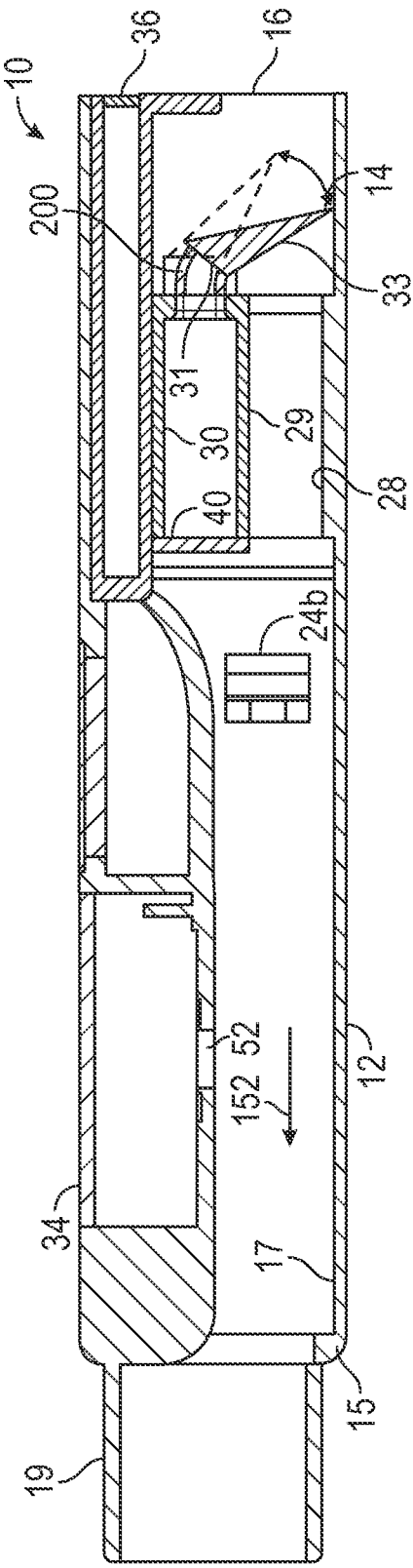
FIG. 9
FIG. 10

NEBULIZER WITH FLUTTER VALVE

This application claims priority to U.S. Provisional Application Ser. No. 62/859,981, filed on Jun. 11, 2019, the entirety of which is hereby expressly incorporated herein by reference.

BACKGROUND

A nebulizer is a drug delivery device used to administer medication in the form of a mist inhaled into the lungs. Nebulizers are commonly used to treat asthma, cystic fibrosis, COPD, and other respiratory diseases or disorders.

Nebulizers for introduction of medication to or irrigation of the nasal passages generally comprise an air compressor, a nebulizer cup for medication, and compressor tubing to connect the compressor to the nebulizer cup. To use the nebulizer, the compressor must be placed on a sturdy surface to support its weight and its power supply cord must be plugged into an outlet. In general, the compressor is not a portable or lightweight device.

It would be desirable to have a nebulizer that allows for more convenient use not requiring connecting tubing, a power supply cord, or a heavy or bulky compressor. Therefore, a need exists for small, portable nebulizer that overcomes the shortcomings of the present designs. It is to such a nebulizer that the inventive concepts disclosed herein are directed.

BRIEF DESCRIPTION OF THE DRAWINGS

FIG. 9 is a cross-sectional view of the nebulizer of FIG. 1 shown in a flutter mode.

FIG. 10 is a cross-sectional view of the nebulizer of FIG. 1 shown in a non-flutter mode.

DETAILED DESCRIPTION OF EXEMPLARY EMBODIMENTS

The inventive concepts are generally directed to a nebulizer that includes a body having a first end, a second end, an aerosol delivery channel extending through the body from the first end to the second end, and a fluid reservoir receiving compartment in communication with the aerosol delivery channel. The first end of the body has a mouthpiece. A fluid reservoir is positioned in the fluid reservoir receiving compartment. The fluid reservoir contains a volume of fluid and has a mesh disc for delivering the fluid to the aerosol delivery channel in an aerosol form upon the mesh disc being energized. A flutter valve is positioned in the aerosol delivery channel of the body near the second end of the body. The flutter valve is moveable between a closed position on inhalation via the mouthpiece and an open position when an expiratory pressure greater than a predetermined expiratory pressure is exerted on the flutter valve.

Before explaining at least one embodiment of the inventive concepts disclosed, it is to be understood that the inventive concepts are not limited in their application to the details of construction and the arrangement of the components or steps or methodologies in the following description or illustrated in the drawings. The inventive concepts disclosed are capable of other embodiments or of being practiced or carried out in various ways. Also, it is to be understood that the phraseology and terminology employed is for description only and should not be regarded as limiting the inventive concepts disclosed and claimed herein.

In this detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, well-known features may not be described to avoid unnecessarily complicating the disclosure.

Further, unless stated to the contrary, "or" refers to an inclusive "or" and not to an exclusive "or." For example, a condition A or B is satisfied by anyone of: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts disclosed. This description should be read to include one or at least one and the singular also includes the plural unless it is obvious that it is meant otherwise.

As used herein any reference to "one embodiment" or "an embodiment" means that a particular element, feature, structure, or characteristic described in the embodiment is included in at least one embodiment. The appearances of the phrase "in one embodiment" in various places in the specification are not necessarily all referring to the same embodiment.

Referring now to the drawings, and particularly to FIGS. 1, 2, 9, and 10, a nebulizer 10 constructed in accordance with the inventive concepts disclosed herein is illustrated. Broadly, the nebulizer 10 includes a body 12, a fluid reservoir 13, and a flutter valve 14.

The body 12 may be an elongated, pen-like structure with a first end 15, a second end 16, an aerosol delivery channel 17 extending through the body 12 from the first end 15 to the second end 16, and a fluid reservoir receiving compartment 18 in communication with the aerosol delivery channel 17. The first end 15 of the body 12 has a mouthpiece 19, which may be formed as part of the body 12 or connected to the body 12. The mouthpiece 19 may be formed in a variety of shapes. For example, as depicted in FIGS. 1, 13A, and 13B, the mouthpiece 19 may be generally square shaped, or as depicted in FIGS. 9 and 10 the mouthpiece 19 may be generally cylindrically shaped. The body 12 may be formed of any suitable metals or plastics.

Figure 1:
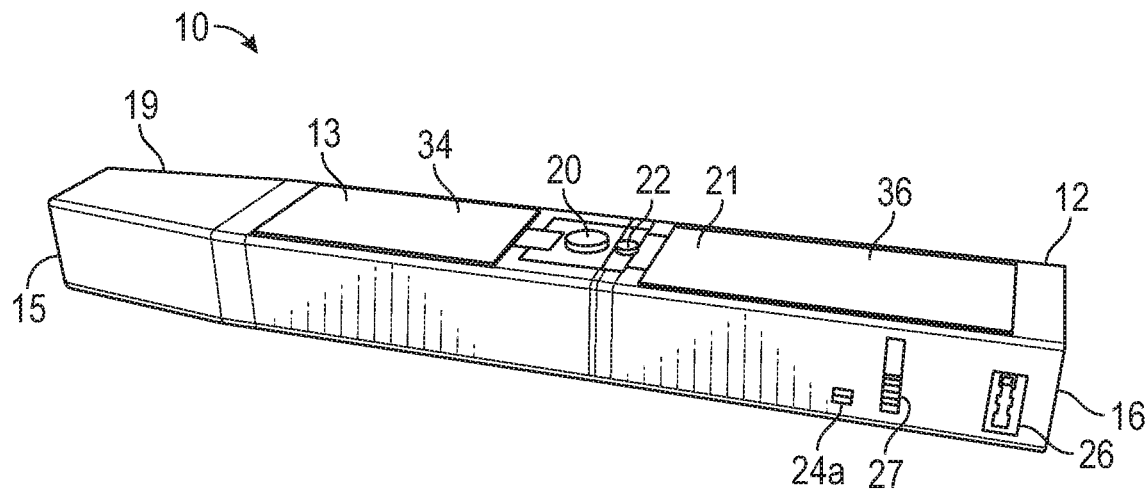
FIG. 1 is a perspective view of a nebulizer constructed in accordance with one embodiment of the inventive concepts disclosed herein.

The body 12 further includes an electronics compartment 21 and a pair of side vents 24*a* and 24*b* (only one of which can be seen in FIG. 1). The body 12 supports a power switch 20, a power indicator 22, a valve switch 26, and a channel switch 27.

A first cover 34 covers the fluid reservoir receiving compartment 18 and a second cover 36 covers the electronics compartment 21. The first cover 34 and the second cover 36 may be hinged or removable to allow access to the fluid reservoir receiving compartment 18 and the electronics compartment 21, respectively. The first cover 34 and the second cover 36 may have closure mechanisms (not shown), such as latches, magnets, or screws that secure the first cover 34 and the second cover 36 in a closed position. In some embodiments, the first cover 34 may be clear to allow a user to visualize the contents of the fluid reservoir receiving compartment 18. The second cover 36 may include a gasket (not shown) that seats in the electronics compartment 21 when the second cover 36 is closed to form a waterproof seal which prevents liquid from entering the electronics compartment 21.

Figure 2:
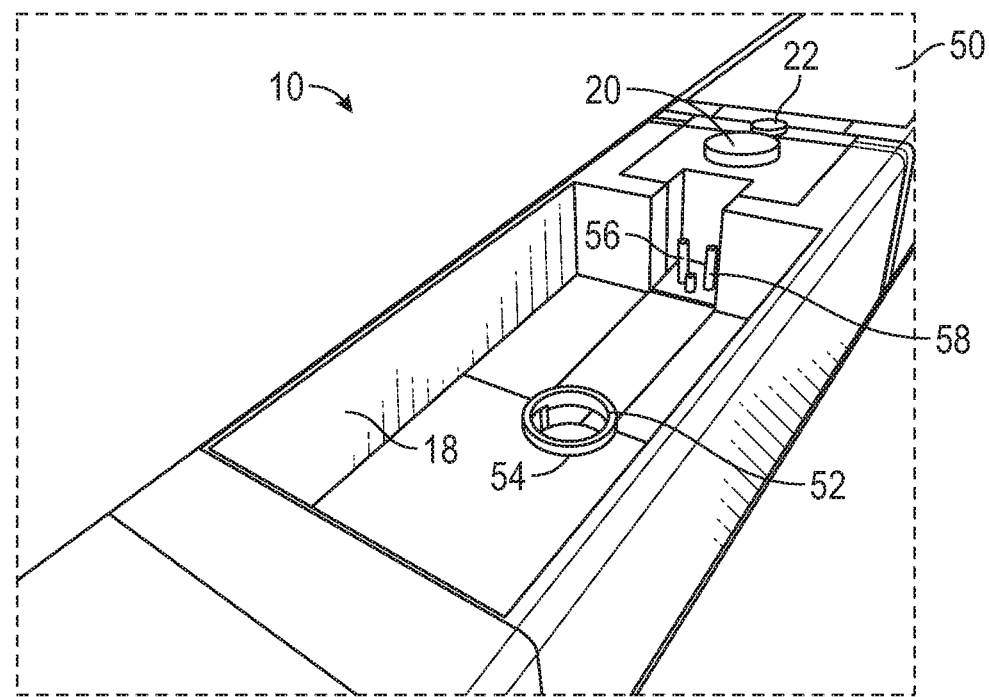
FIG. 2 is a perspective view of the nebulizer of FIG. 1 with a first cover of a fluid reservoir receiving compartment removed.

Referring now to FIG. 2, the electronics compartment 21 houses electronic components of the nebulizer 10, such as a battery 50 shown seated in the electronics compartment 21. The battery 50 provides power to the nebulizer 10. The battery 50 may be any rechargeable-type battery, such as a lithium ion battery. The battery 50 may be charged using a wired connection (not shown) such as USB-c or wirelessly using inductive coils (not shown).

If the battery 50 is wirelessly charged, a wireless charging hub (not shown) may be provided that the nebulizer 10 may be seated in for charging. The wireless charging hub will be constructed so the nebulizer 10 seats into the wireless charging hub in an upright manner to allow draining/escape of any liquid residual that may flow from the nebulizer 10 after use. The wireless charging hub may have a small hole in the bottom of the formed structure that will allow for draining/escape of any liquid residual that may flow from the nebulizer 10 after use. The wireless charging hub may have a USB connection that will attach to a universal plug adapter or an optional cigarette lighter adapter for use in vehicles.

The nebulizer 10 may further be provided with an electric current controller (not shown), electrical connections between the battery 50 and the electrical current controller, and electrical current leads that extend into the fluid reservoir receiving compartment 18. The power indicator 22 may be an LED that indicates whether the nebulizer 10 is on or off as well as charge status of the battery 50.

The fluid reservoir receiving compartment 18 is provided with an aperture 52 extending from the fluid reservoir receiving compartment 18 into the aerosol delivery channel 17. A gasket 54 forms a seal between the fluid reservoir receiving compartment 18 and the aerosol delivery channel 17 when the fluid reservoir 13 (FIG. 3) is inserted in the fluid reservoir receiving compartment 18. The aperture 52 directs an aerosolized fluid from the fluid reservoir 13 into the aerosol delivery channel 17, as described further herein.

Electrical leads 56 and 58 connect to electrical leads 72 and 74 (FIG. 3) of the fluid reservoir 13 thereby connecting the fluid reservoir 13 with the battery 50 to provide power to the fluid reservoir 13 when the power switch 20 is in an on position.

Figure 3:
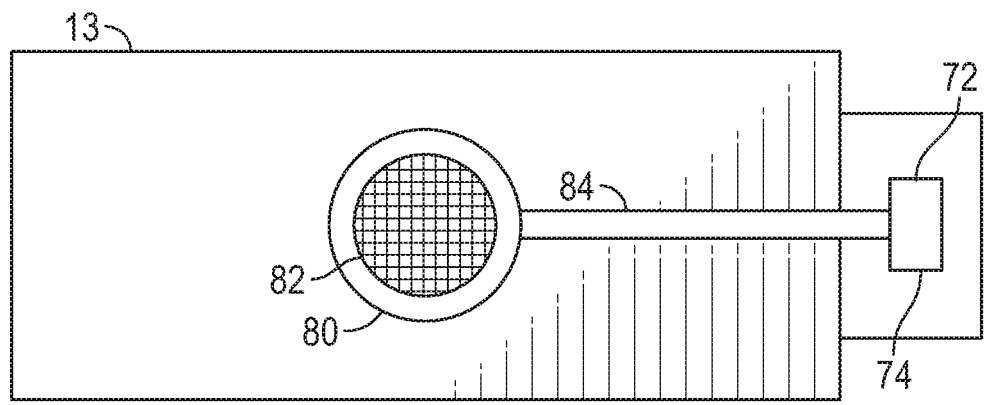
FIG. 3 is a bottom plan view of a fluid reservoir.
Figure 4:
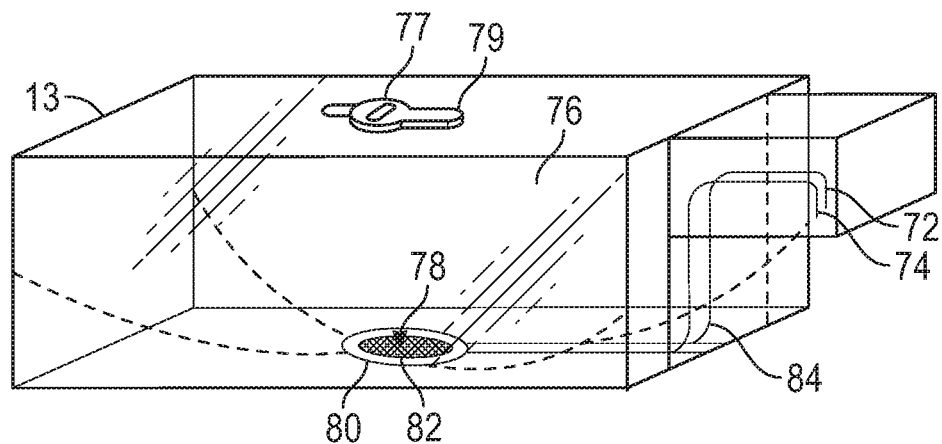
FIG. 4 is a diagrammatic, perspective view of the fluid reservoir of FIG. 3.
Figure 5:
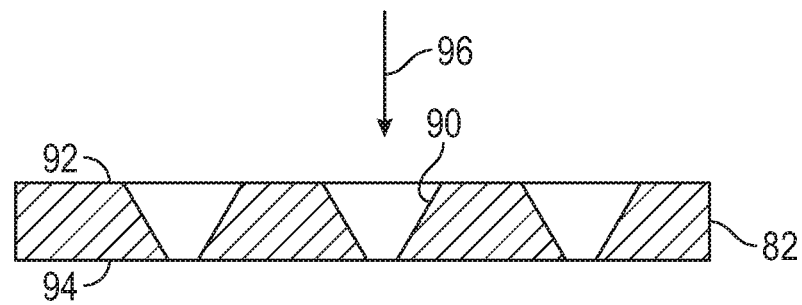
FIG. 5 is a cross-sectional view of a vibrating mesh disc.

Referring now to FIGS. 3-5, shown is the fluid reservoir 13. The fluid reservoir 13 is sized and shaped to be positioned in the fluid reservoir receiving compartment 18 of the body 12. The fluid reservoir 13 is provided with electrical leads 72 and 74, a fill aperture 77, an outlet aperture 78, an electric actuator 80, a vibrating mesh disc 82 connected to the electric actuator 80, and an electrical lead 84 connecting electrical leads 72 and 74 and the electric actuator 80.

The fluid reservoir 13 may be filled with a fluid, such as a medication or suspension, using the fill aperture 77. The fill aperture 77 may be sealed with a cap 79 or plug once the fluid reservoir 13 is filled. In some embodiments, fluid reservoir 13 may be disposable. The interchangeable nature of fluid reservoir 13 allows a user to dispense various types of medications by switching the fluid reservoir 13 for another fluid reservoir 13 containing a different medication.

The fluid reservoir 13 may be sized to hold a predetermined amount of fluid. For instance, the fluid reservoir 13 may hold fluid for a prescribed dosage of medication for a predetermined amount of time such as a week, two weeks, three weeks, or a month. Alternatively, the fluid reservoir 13 may hold a predetermined volume of fluid between 1 ml and 10 ml.

The fluid reservoir 13 may be shaped to direct fluid to the vibrating mesh disc 82. For instance, as seen in FIG. 4 the fluid reservoir 13 may have angled surfaces that direct fluid to the vibrating mesh disc 82 when the nebulizer 10 is held in an operating orientation.

To aerosolize the fluid, an electrical current is supplied to the electric actuator 80 which causes the vibrating mesh disc 82, which is formed of a piezoelectric material, to vibrate at a high rate of speed so fluid is drawn through apertures 90 to form droplets of consistent size that are delivered at a low velocity though the aperture 52 of the fluid reservoir receiving compartment 18 and into the aerosol delivery channel 17. The apertures 90 may have a conical shape with the largest cross-section of the cone in contact with the fluid in the fluid reservoir 76. In other words, a first side 92 of the vibrating mesh disc 82 is in the fluid reservoir 76 while a second side 94 of the vibrating mesh disc 82 aligns with and faces the aperture 52 of the fluid reservoir receiving compartment 18 when the fluid reservoir 13 is inserted in the fluid reservoir receiving compartment 18. Fluid passes through the vibrating mesh disc 82 in the direction of arrow 96.

Referring now to FIGS. 9 and 10, the aerosol delivery channel 17 extends the length of the body 12 from the first end 15 to the second end 16. The flutter valve 14 is positioned in the aerosol delivery channel of the body 12 near the second end 16 of the body 12. The flutter valve 14 is placed in the aerosol delivery channel 17 and situated so the flutter valve 14 is normally in closed position when the nebulizer 10 is operably oriented. For instance, in the embodiment illustrated in FIGS. 9 and 10, the flutter valve 14 is pivotally attached to the body 12 and angled so gravity causes the flutter valve 14 to close when the nebulizer 10 is operably oriented. When air traveling in a direction indicated by arrow 152 is pulled through the nebulizer 10, negative pressure is generated and the flutter valve 14 will be closed. When air traveling in a direction indicated by arrow 150 is pushed through the nebulizer 10, positive pressure causes the flutter valve 14 to open and allow the air to pass out the second end 16.

In one embodiment illustrated in FIGS. 9 and 10, the aerosol delivery channel 17 is provided with a divider 29 that bifurcates the aerosol delivery channel 17 into a first channel 28 and a second channel 30. The second channel 30 forms a plenum that directs air to a first face 31 of the flutter valve 14. The second channel 30 may include a distal plenum portion 200 of reduced diameter relative to the remainder of the channel 30. The plenum portion 200 may have a distal end 202 angled and configured to compliment the first face 31 of the of the flutter valve 14 so a backpressure is created in the second channel 30 when the flutter valve 14 is in the closed position.

Figure 11:
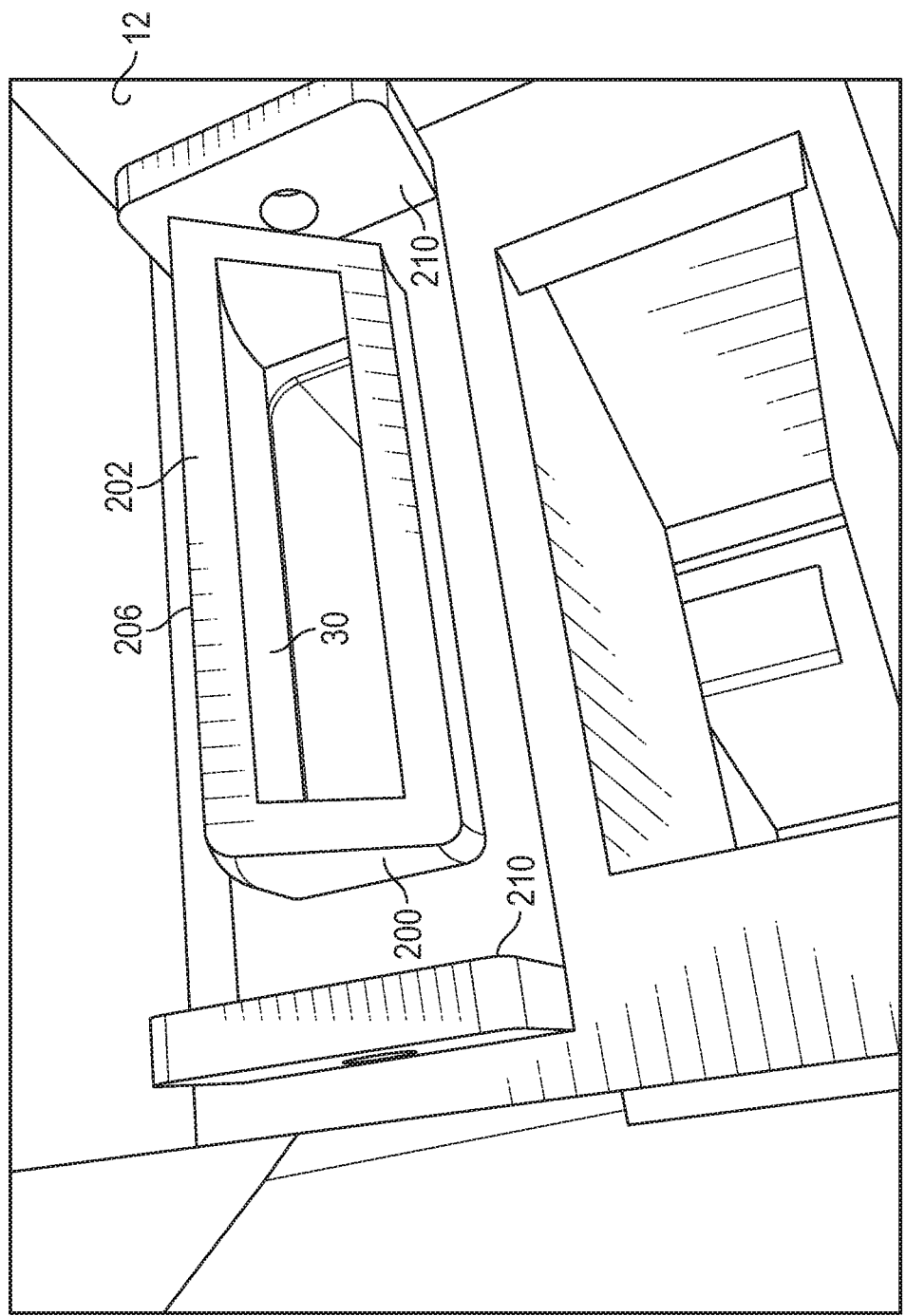
FIG. 11 is a perspective view of the nebulizer with a flutter valve removed for clarity.
Figure 12A:
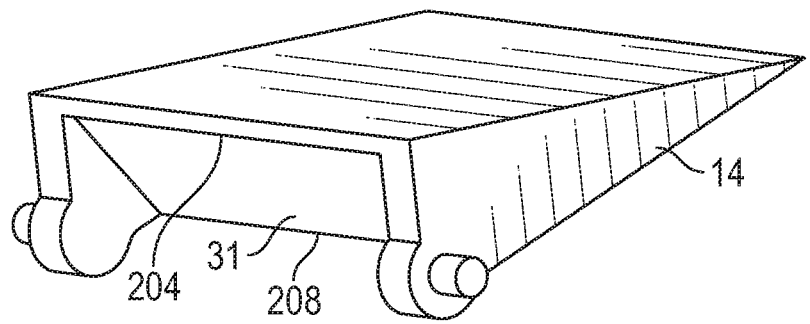
FIG. 12A is a top perspective view of one embodiment of a flutter valve.
Figure 12B:
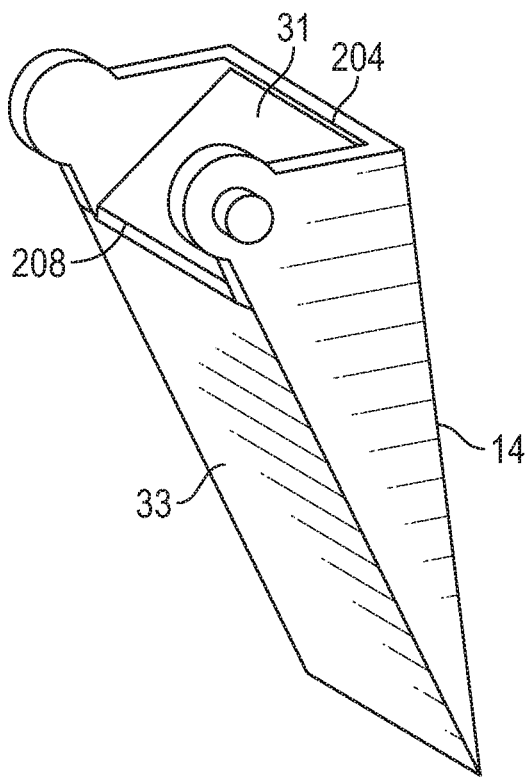
FIG. 12B is a bottom perspective view of the flutter valve of FIG. 12A.
Figure 13A:
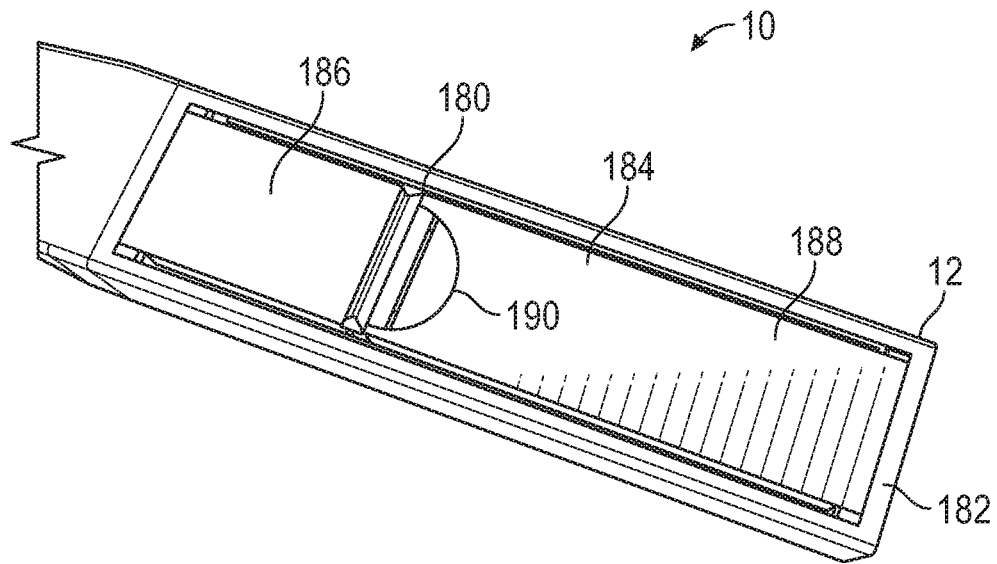
FIG. 13A is a bottom perspective view of the nebulizer of FIG. 1 with a handle in a closed position.
Figure 13B:
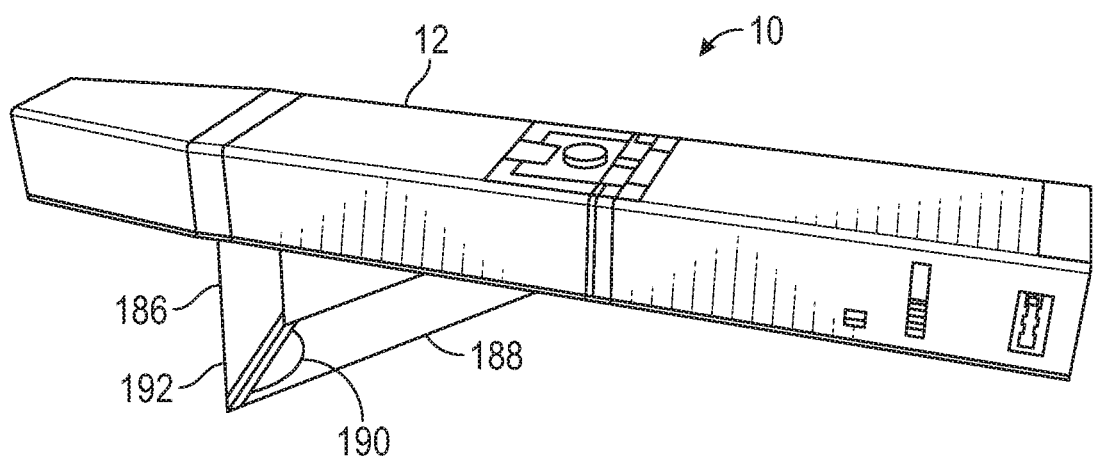
FIG. 13B is a perspective view of the nebulizer of FIG. 1 with the handle in an open position.

The flutter valve 14 may be formed in a variety of shapes. One example of a suitable flutter valve is disclosed in U.S. Pat. No. 10,004,772, which is hereby expressly incorporated herein by reference. In one embodiment and as best shown in FIGS. 12A and 12B, the first face 31 of the flutter valve 14 may have an upper lip 204 positionable over an upper edge 206 of the plenum portion 200 to facilitate rotation of the flutter valve 14 to the open position. The first face 31 may also have a beveled lower edge 208 to permit air leakage past the first face 31 in a way that causes the flutter valve 14 to oscillate. The flutter valve 14 may be pivotally attached to the housing 12 via a pair of bosses 200 (FIG. 11).

A gate 40 attached to the channel switch 27 may be selectively positioned in the first channel 28 or the second channel 30 to selectively direct air into the first channel 28 or the second channel 30. For instance, as illustrated in FIGS. 9 and 10, the gate 40 is positioned in the first channel 28 so exhaled air is directed into the second channel 30 and against the first face 31 of the flutter valve 14. When exhaled air is directed to the first face 31 of the flutter valve 14, the positive pressures generated during exhalation will cause the flutter valve 14 to have a fluttering or oscillating action. This fluttering causes increased pressure within aerosol delivery channel 17 which, with a seal on the mouthpiece 19 by the user, provides an oscillatory positive expiratory pressure. The side vents 24a and 24b allow air to be drawn in as the user inhales, but not when the user exhales. The user must exhale harder against the resistance of the flutter valve 14. It takes approximately four times as long to exhale against the resistance of the flutter valve 14 than it does to inhale. This oscillatory positive expiratory pressure helps air push mucus trapped in the lungs and airways, for instance, and helps move the mucus from lung and airway walls. The oscillatory positive expiratory pressure also holds the user's airways open. The expiratory air pressures needed to open the flutter valve 14 may be in a range of about 10 cm $H_2O$ and about 30 cm $H_2O$. However, in some embodiments the expiratory air pressure needed to open the flutter valve 14 may be less than 10 cm $H_2O$ and greater than 30 cm $H_2O$.

When the gate 40 is positioned in the second channel 30 (FIG. 10), exhaled air is directed into the first channel 28 and against the second face 33 of the flutter valve 14. When exhaled air is directed to the second face 33 of the flutter valve 14, the positive pressures generated during exhalation needed to open the flutter valve 14 are less than about 10 cm $H_2O$. Further, the flutter valve 14 does not flutter when the exhaled air is directed to the second face 33 of the flutter valve 14.

Using the channel switch 27 connected to the gate 40, the user may alternate between non-flutter mode and flutter mode which causes oscillations in expiratory air exhaled by a user and transmitting the oscillations throughout the lungs and airways of the user.

To facilitate sealing of the flutter valve 14, a gasket (not shown) may be included to create an airtight seal when the flutter valve 14 is in the closed position.

By way of illustration, when the power switch 20 is actuated, the vibrating mesh disc 82 of the fluid reservoir 13 will aerosolize liquid in the fluid reservoir 13 and expel the aerosolized liquid into the aerosol delivery channel 17 where the aerosolized liquid is available to be inhaled by a user. The flutter valve 14 will remain closed to assist holding the aerosolized liquid in the aerosol delivery channel 17. Upon a user placing her lips around the mouthpiece 19 and inhaling, the flutter valve 14 is closed and air will be drawn into the aerosol delivery channel 17 through the side vents 24a and 24b and mixed with the aerosolized liquid. The mixed aerosolized liquid and air will be drawn through the aerosol delivery channel 17 and into the user's airway. When the user exhales, or pushes air in the direction of arrow 104, the flutter valve 14 will open to expel excess aerosolized fluid and the exhaled air.

Because the aerosol delivery channel 17 runs the length of the nebulizer 10 from the first end 15 to the second end 16, a greater volume of aerosolized fluid may fill the aerosol delivery channel 17 before inhalation. This allows for a greater volume of aerosolized fluid, or a reserve of aerosolized fluid, to be readily available upon inhalation by the user therefore potentially delivery more medication per breath.

Figure 6:
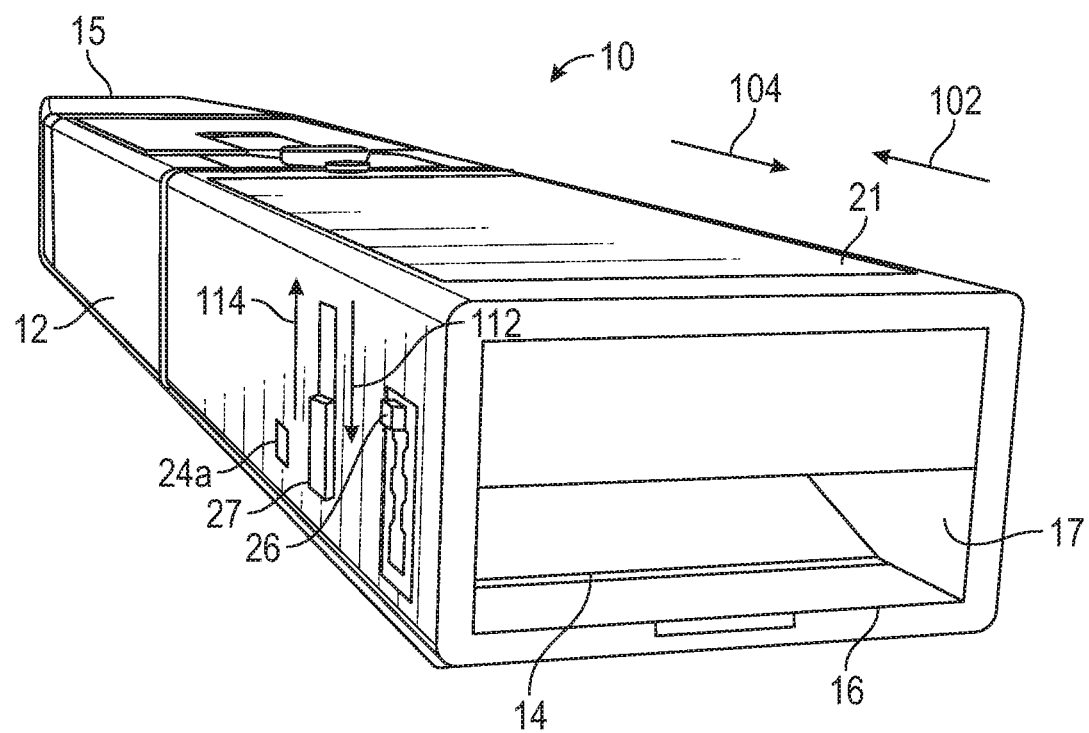
FIG. 6 is a rear perspective of the nebulizer of FIG. 1.
Figure 7:
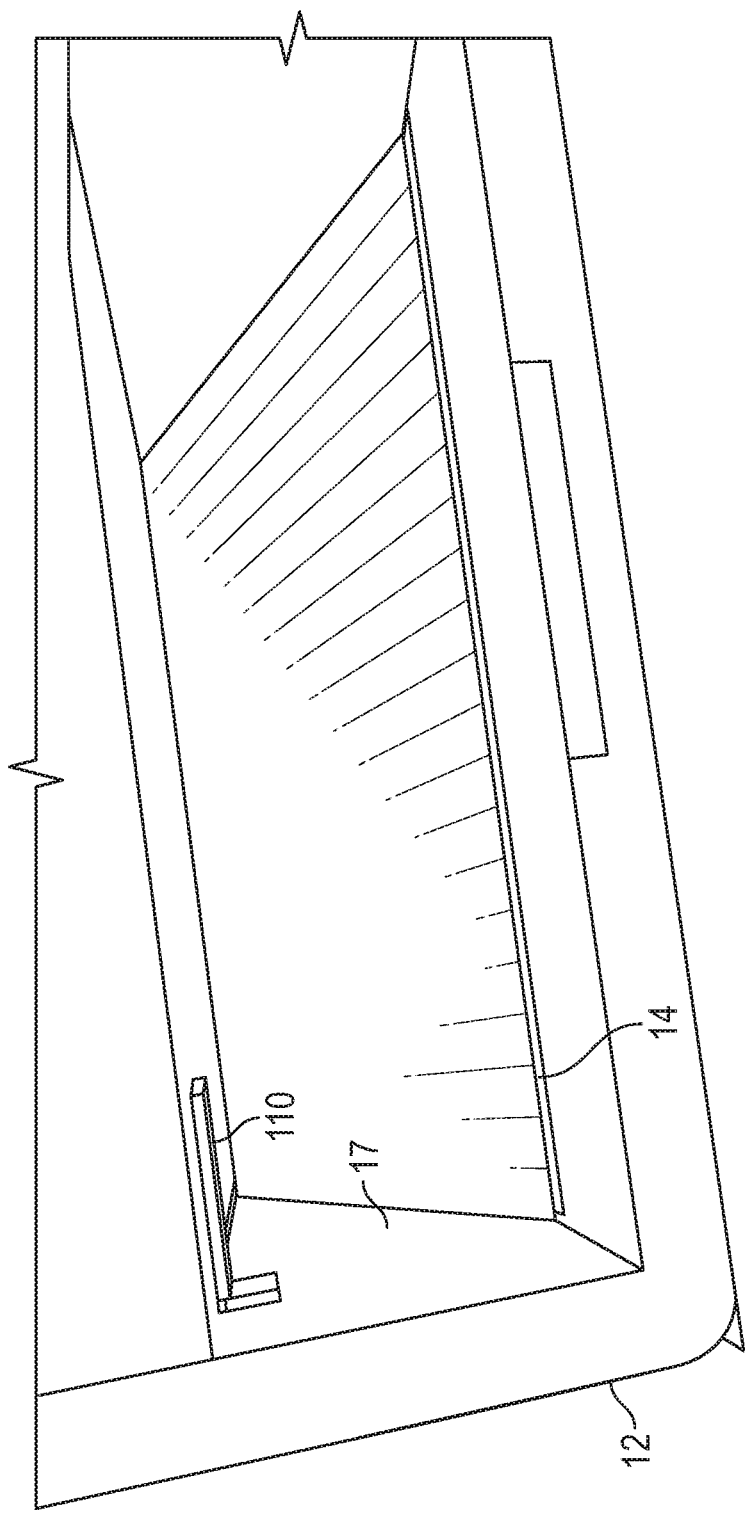
FIG. 7 is a rear perspective view of the nebulizer showing an adjustable arm that controls a flutter valve of the nebulizer of FIG. 1.

Referring now to FIGS. 6 and 7, an arm 110 extends at least partially into the aerosol delivery channel 17 and is attached to the flutter valve switch 26. The arm 110 selectively restricts how far the flutter valve 14 can open, thus restricting the volume of air that can be expelled through the aerosol deliver channel 17. For instance, when the flutter valve switch 26 is in a first position (illustrated in FIG. 6), the flutter valve 14 will open fully when the user exhales with an expiratory air pressure in the direction of arrow 104 through the aerosol delivery channel 17. When the flutter valve switch 26 is moved in the direction of arrow 112, the arm 110 decreases how far the flutter valve 14 will open, thus requiring a longer amount of time to expel the same volume of air from the user's respiratory system. An amount of restriction can be varied by moving the flutter valve switch 26 in the direction indicated by arrow 112 for more restriction, or moving the flutter valve switch 26 in a direction indicated by arrow 114 for less restriction. In this way, the restriction provided against the flutter valve 14 is adjustable so the expiratory air volume that may pass through the aerosol delivery channel 17 may be varied. The expiratory air pressures recited are for illustration only and the arm 110 may bias the flutter valve 14 so the expiratory air pressure needed to open the flutter valve is less than 10 cm $H_2O$ and greater than 30 cm $H_2O$.

Figure 8:
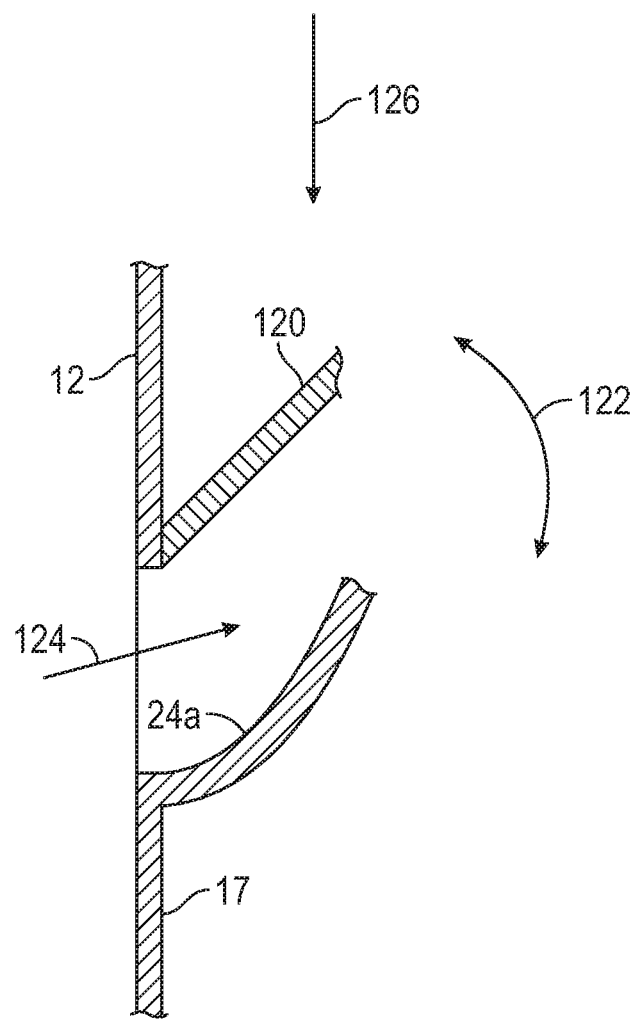
FIG. 8 is a cross-sectional view of a side vent of the nebulizer of FIG. 1.

Referring now to FIG. 8, one embodiment of the side vent 24a is illustrated formed in the body 12 of the nebulizer 10. The side vent 24a extends through the body 12 and into the aerosol delivery channel 17 as described above. The side vent 24a is provided with a check valve 120 that may be hinged to open and close as indicated by arrow 122. The check valve 120 opens when air is drawn into the aerosol delivery channel 17 as indicated by arrow 124. Air is drawn into the aerosol delivery channel 17 when the user places their mouth on the mouthpiece 19 and inhales. When the user exhales into the mouthpiece 19, air travelling through the aerosol delivery channel 17 in direction 126 causes the check valve 120 to close. Closure of the check valve 120 forces exhaled air through the aerosol delivery channel 17 and past the flutter valve 14 which may be set to provide oscillatory positive expiratory pressure as described above.

Referring now to FIGS. 12A and 12B, the body 12 may have a track 180 that protrudes from the body 12 of the nebulizer 10 on a bottom side 182. This track 180 may have a slide 184 constructed of a first piece 186 and a second piece 188 that when closed or disengaged will lay flat against the body 12 of the nebulizer 10 in a retracted position. The user will be able, via a small opening 190 or finger slot, to engage the slide 184 away from the body 12 to form a V-shaped handle 192 in an extended position. The purpose of this V-shaped handle 192 will be to give the user the option of added stability while holding the nebulizer 10. This V-shaped handle 192 when engaged, will allow the user to use multiple fingers or their entire hand to hold the nebulizer 10 body 12 and V-shaped handle 192 giving the user added stability and ease of handling during use.

The first piece 186 of the slide 184 can be removed completely from the track 180 by disengaging the first piece 186 from the track 180. Once removed from the track 180, the second piece 188 and from slide component can be made into a straight piece and inverted in orientation so the front slide piece is not positioned towards the back and under side of the nebulizer. This option allows the first piece 186 to click into or engage into a clip holder (not shown) on an optional aerosol face mask (not shown). The optional face mask can accept the mouthpiece 16 of the nebulizer 10 into an opening on the aerosol face mask that will securely hold the nebulizer 10 into the mask. The first piece 186 of the slide 180, once inverted toward the back and bottom side 182 of the nebulizer 10, will attach to an adapter (not shown) that engages the first piece 186 of the slide 180 on a portion of the aerosol face mask. This option is incorporated to give the nebulizer user the ability to use an aerosol face mask with nebulizer 10 and have two points of contact for added stability. After use, the front piece 186 of the slide 182 can be disengaged from the aerosol mask and re-engaged onto the bottom side 182 of the nebulizer 10, sliding back into the track 180 and retracted into the formed track 180 on the bottom side 182 of the nebulizer 10.

While the nebulizer 10 has been illustrated with the mouthpiece 19, in some embodiments (not shown) the mouthpiece 19 may be replaced with a mask, for instance, or other device that provides a seal against or in a user's mouth to allow increased inspiration velocity of an aerosolized fluid and air mixture upon inhalation as described above.

From the above description, it is clear that the inventive concepts disclosed herein is well adapted to carry out the objects and to attain the advantages mentioned herein as well as those inherent in the inventive concepts disclosed herein. While exemplary embodiments of the inventive concepts disclosed herein have been described for purposes of this disclosure, it will be understood that numerous changes may be made which will readily suggest themselves to those skilled in the art and which are accomplished within the scope and coverage of the inventive concepts disclosed and claimed herein.

What is claimed is:

1. A nebulizer, comprising:
   a body having a first end, a second end, an aerosol delivery channel extending through the body from the first end to the second end, and a fluid reservoir receiving compartment in communication with the aerosol delivery channel, the first end of the body having a mouthpiece;
   a fluid reservoir positioned in the fluid reservoir receiving compartment, the fluid reservoir containing a volume of fluid and having a vibrating mesh disc for delivering the fluid to the aerosol delivery channel in an aerosol form upon the vibrating mesh disc being energized; and
   a flutter valve positioned in the aerosol delivery channel of the body near the second end of the body, the flutter valve moveable between a dosed position and an open position when an expiratory pressure of exhaled air greater than a predetermined expiratory pressure is exerted on the flutter valve,
   wherein the aerosol delivery channel has a divider and a gate, the divider is positioned so the aerosol delivery channel comprises a first channel and a second channel, the flutter valve is positioned in the second channel, and the gate is positionable between the first channel and the second channel to selectively direct the exhaled air into one of the first channel and the second channel when the exhaled air is flowing through the aerosol delivery channel toward the second end,
   wherein the flutter valve has a first face and a second face angled relative to the first face, and wherein the first face is positioned over the second channel and the second face is positioned over the first channel, and
   wherein the fluid reservoir receiving compartment intersects the aerosol delivery channel between the mouthpiece and the gate.

2. The nebulizer of claim 1, wherein the flutter valve is pivotally connected to the body and oscillates between the closed position and the open position when the exhaled air is flowing through the aerosol delivery channel toward the second end of the body.

3. The nebulizer of claim 1, further comprising a valve switch supported by the body and operably connected to the flutter valve to adjust the predetermined expiratory pressure necessary to open the flutter valve.

4. The nebulizer of claim 3, further comprising an arm connected to the valve switch and extending at least partially into the aerosol delivery channel to limit the movement of the flutter valve from the closed position to the open position.

5. The nebulizer of claim 1, wherein the first face of the flutter valve has an upper edge with a Up and a lower beveled edge.

6. The nebulizer of claim 1, wherein the predetermined expiratory pressure is in a range of 10 cm $H_2O$ to 30 cm $H_2O$ when the gate is in the first channel and the predetermined expiratory pressure is less than 10 cm $H_2O$ when the gate is in the second channel.

7. The nebulizer of claim 1, wherein the fluid reservoir holds a volume of fluid between 1 ml and 10 ml.

8. The nebulizer of claim 1, wherein the body has at least one side vent and a check valve positioned over the side vent to allow inhaled air to flow through the at least one side vent and into the aerosol delivery channel but prevent exhaled air from flowing from the aerosol delivery channel through the at least one side vent.

9. The nebulizer of claim 1, further comprising a clear cover covering the fluid reservoir receiving compartment.

10. The nebulizer of claim 1, wherein the body has a handle.

11. The nebulizer of claim 10, wherein the handle is movable between a retracted position and an extended position.

12. The nebulizer of claim 11, wherein the handle has a first piece and a second piece forming a V-shape in the extended position.

13. The nebulizer of claim 1, wherein the body is generally pen-shaped.

14. A nebulizer, comprising:
   a body having a first end, a second end, an aerosol delivery channel extending through the body from the first end to the second end, and a fluid reservoir receiving compartment in communication with the aerosol delivery channel, the first end of the body having a mouthpiece;

a fluid reservoir positioned in the fluid reservoir receiving compartment, the fluid reservoir containing a volume of fluid and having a vibrating mesh disc for delivering the fluid to the aerosol delivery channel in an aerosol form upon the vibrating mesh disc being energized; and a flutter valve positioned in the aerosol delivery channel of the body near the second end of the body, the flutter valve moveable between a closed position and an open position when an expiratory pressure of exhaled air greater than a predetermined expiratory pressure is exerted on the flutter valve, wherein the aerosol delivery channel has a divider and a gate, the divider is positioned so the aerosol delivery channel comprises a first channel and a second channel, and the gate is positionable between the first channel and the second channel to selectively direct the exhaled air into one of the first channel and the second channel when the exhaled air is flowing through the aerosol delivery channel toward the second end, and wherein the flutter valve has a first face and a second face angled relative to the first face, and wherein the first face is positioned over the second channel and the second face is positioned over the first channel.

15. The nebulizer of claim 14, wherein the first face of the flutter valve has an upper edge with a lip and a lower beveled edge.

16. The nebulizer of claim 14, wherein the body has at least one side vent and a check valve positioned over the side vent to allow inhaled air to flow through the at least one side vent and into the aerosol delivery channel but prevent exhaled air from flowing from the aerosol delivery channel through the at least one side vent.

17. The nebulizer of claim 14, further comprising a clear cover covering the fluid reservoir receiving compartment.

18. The nebulizer of claim 14, wherein the body has a handle.

19. The nebulizer of claim 18, wherein the handle is movable between a retracted position and an extended position.

20. The nebulizer of claim 14, wherein the body is generally pen-shaped.

* * * * *

UNITED STATES PATENT AND TRADEMARK OFFICE
CERTIFICATE OF CORRECTION

| | |
|---|---|
| PATENT NO. | : 11,813,397 B2 |
| APPLICATION NO. | : 16/898762 |
| DATED | : November 14, 2023 |
| INVENTOR(S) | : Justin Rowley |

It is certified that error appears in the above-identified patent and that said Letters Patent is hereby corrected as shown below:

In the Claims

Column 7, Line 66: Delete "dosed" and replace with -- closed --

Column 8, Line 34: Delete "Up" and replace with -- lip --

Column 9, Line 8: Delete "dosed" and replace with -- closed --

Signed and Sealed this
Nineteenth Day of December, 2023

Katherine Kelly Vidal
*Director of the United States Patent and Trademark Office*